(12) United States Patent
Smargiassi (10) Patent No.: US 7,935,940 B1
(45) Date of Patent: May 3, 2011

(54) MEASURING IN-SITU UV INTENSITY IN UV CURE TOOL

(75) Inventor: Eugene Smargiassi, Tualatin, OR (US)

(73) Assignee: Novellus Systems, Inc., San Jose, CA (US)

( * ) Notice: Subject to any disclaimer, the term of this patent is extended or adjusted under 35 U.S.C. 154(b) by 381 days.

(21) Appl. No.: 12/008,149

(22) Filed: Jan. 8, 2008

(51) Int. Cl.
*H01J 37/00* (2006.01)

(52) U.S. Cl. ........................ 250/492.1; 362/243; 315/291

(58) Field of Classification Search ................ 250/492.1
See application file for complete search history.

(56) References Cited

U.S. PATENT DOCUMENTS

| | | | |
|---|---|---|---|
| 3,504,181 A * | 3/1970 | Campbell et al. .......... 250/336.1 |
| 4,563,589 A | 1/1986 | Scheffer |
| 4,872,947 A | 10/1989 | Wang et al. |
| 5,166,101 A | 11/1992 | Lee et al. |
| 5,178,682 A | 1/1993 | Tsukamoto et al. |
| 5,282,121 A | 1/1994 | Bornhorst et al. |
| 5,354,715 A | 10/1994 | Wang et al. |
| 5,426,076 A | 6/1995 | Moghadam et al. |
| 5,518,959 A | 5/1996 | Jang et al. |
| 5,674,783 A | 10/1997 | Jang et al. |
| 6,394,797 B1 | 5/2002 | Sugaya et al. |
| 6,467,491 B1 | 10/2002 | Sugiura et al. |
| 6,530,380 B1 | 3/2003 | Zhou et al. |
| 6,563,092 B1 | 5/2003 | Shrinivasan et al. |
| 6,629,012 B1 * | 9/2003 | Riley et al. ..................... 700/121 |
| 7,067,819 B2 * | 6/2006 | Janik .............................. 250/372 |
| 7,087,497 B2 | 8/2006 | Yuan et al. |
| 7,638,780 B2 * | 12/2009 | Kilburn et al. ............. 250/492.1 |
| 7,704,894 B1 | 4/2010 | Henry et al. |
| 2002/0117109 A1 | 8/2002 | Hazelton et al. |
| 2003/0013280 A1 | 1/2003 | Yamanaka |
| 2003/0194493 A1 | 10/2003 | Chang et al. |
| 2004/0023513 A1 | 2/2004 | Aoyama et al. |
| 2005/0196929 A1 | 9/2005 | Yuan et al. |

FOREIGN PATENT DOCUMENTS
JP 01-107519 4/1989

OTHER PUBLICATIONS

U.S. Appl. No. 11/115,576, "Single-Chamber Sequential Curing of Semiconductor Wafers", Shrinivasan et al., filed Apr. 26, 2005.
U.S. Appl. No. 11/115,576, Office Action mailed Oct. 3, 2007.
U.S. Appl. No. 11/115,576, Office Action mailed May 2, 2008.
U.S. Appl. No. 11/115,576, Office Action mailed Oct. 17, 2008.
U.S. Appl. No. 11/115,576, Office Action mailed Apr. 22, 2009.
U.S. Appl. No. 11/115,576, Office Action mailed Oct. 1, 2009.

(Continued)

*Primary Examiner* — Phillip A Johnston
(74) *Attorney, Agent, or Firm* — Weaver Austin Villeneuve & Sampson LLP (57) ABSTRACT

Consistent ultraviolet (UV) intensity for a semiconductor UV cure chamber is measured in-situ with a hot pedestal in vacuum by measuring reflected UV light from a calibration substrate at a UV detector mounted in the lamp assembly. The measurement apparatus includes a UV detector, a cover that protects the detector from UV light while not in use, and a mirror disposed between the chamber window and the UV detector. Measured UV intensity from the substrate reflection and from the mirror reflection help determine a course of maintenance action to maintain wafer-to-wafer uniformity.

19 Claims, 6 Drawing Sheets

OTHER PUBLICATIONS

U.S. Appl. No. 11/602,564, "Method of Eliminating Small Bin Defects in High Throughput TEOS Films", Henri et al., filed Nov. 20, 2006.
U.S. Appl. No. 11/602,564, Office Action mailed Feb. 15, 2008.
U.S. Appl. No. 11/602,564, Office Action mailed Sep. 9, 2008.
U.S. Appl. No. 11/602,564, Office Action mailed Mar. 20, 2009.
U.S. Appl. No. 11/602,564, Notice of Allowance mailed Dec. 14, 2009.
U.S. Appl. No. 11/602,564, Allowed Claims.
U.S. Appl. No. 12/001,348, "Tunable-Illumination Reflector Optics for UV Cure System", Bryan Bolt, filed Dec. 10, 2007.
U.S. Appl. No. 11/396,303, "Method of Reducing Defects in PECVD TEOS Films", Dhas et al., filed Mar. 30, 2006.
U.S. Appl. No. 11/396,303, Office Action mailed Dec. 14, 2007.
U.S. Appl. No. 11/396,303, Office Action mailed Aug. 6, 2008.
U.S. Appl. No. 11/396,303, Office Action mailed Mar. 19, 2009.
U.S. Appl. No. 11/396,303, Office Action mailed Oct. 28, 2009.
U.S. Appl. No. 11/115,576, Office Action mailed Apr. 15, 2010.
U.S. Appl. No. 12/726,263, "Apparatus for UV Damage Repair of Low K Films Prior to Copper Barrier Deposition", van Schravendijk, et al., filed Mar. 17, 2010.

* cited by examiner

MEASURING IN-SITU UV INTENSITY IN UV CURE TOOL

FIELD OF THE INVENTION

This invention relates to apparatus and methods for radiation treatment of thin films. More specifically, the invention relates to apparatus and methods to calibrate an ultraviolet radiation apparatus to facilitate a consistent change in film properties.

BACKGROUND

Many layers of thin films are used to make an integrated circuit. IC manufacturing requires thin films to have certain properties in order for the circuit to function as designed. For example, there is a general need for materials with low dielectric constants (low-k). Using low-k materials as the intermetal dielectric (i.e., the layer of insulator separating consecutive levels of the conductive metal interconnects) reduces the delay in signal propagation due to capacitive effects, otherwise know as the RC delay. A dielectric material of low dielectric constant will have low capacitance, and hence the RC delay of an IC constructed with such a material will be lower as well.

As another example, there is a general need for materials with specific tensile or compressive stresses. Increasing shallow trench isolation (STI) film tensile stress increases transistor drain current and device performance because the electron and hole mobilities are higher. Other applications require dielectric films to have compressive stress. These and other properties may be met on the film as deposited, or after treatment.

One such treatment may be a thermal process in which the substrate is heated to a temperature for a time. A thermal treatment may remove unwanted particles from the film, or change its stresses and other properties. These thermal processes, however, have certain difficulties. In particular, substrate temperatures generally need to be high (i.e., greater than about 500 degrees Celsius) with exposure times typically on the order of hours. As is well known in the field, these conditions can damage copper containing devices, especially in the application wherein a low-k dielectric is being cured and the long exposure time may be unsuitable for mass manufacturing. Also, the use of temperature sensitive nickel silicide precludes inducing film stress by using temperatures above 400° C. while some SiN films have a cure temperature up to 480° C.

To overcome these disadvantages of thermal processing, another technique has been developed, which involves curing the film with UV radiation. Irradiation of the low-k or spacer nitride films permits modulation of desired film properties such as dielectric constant or film stress at lower temperatures. However, the use of UV radiation in such processes may result in deleterious side-effects unless special care is taken to deliver the precise amount of radiation and to maintain the substrate temperature at an optimal level. Delivery of the precise amount of radiation may be complicated when UV lamp intensity drifts over time and UV exposure results affect optical parts.

What are needed therefore are improved methods and devices for treating thin films with UV radiation to obtain desired film properties.

SUMMARY

The present invention addresses this need by providing improved apparatus and methods for ultraviolet (UV) cure of thin films. A semiconductor processing apparatus for UV cure involves a process chamber and a UV radiation assembly external to the process chamber. The UV radiation assembly transmits radiation into the chamber on a substrate holder through a chamber window. A UV detector measures UV intensity from time to time. Change in performance of a UV bulb and solarization of and deposits on optical parts affect UV intensity over time. Some UV processing produces outgas material that may deposit on chamber parts such as walls and windows. Window deposits decrease UV intensity as experienced by the substrate. Also, UV lamp output degrades over time, and optical parts may become solarized after exposure. To ensure that the UV cure as experienced by substrates remains constant, a number of corrective action may be taken if the measured UV intensity deviates from an acceptable range.

In one aspect, the present invention pertains to a UV apparatus including a process chamber and a UV radiation assembly mounted on the process chamber. The UV radiation assembly includes one or more UV radiation sources, one or more reflectors operable to direct a portion of the UV radiation through the window towards the substrate holder, and a UV intensity detector. This detector is mounted below the UV lamps and external to the chamber. It is oriented toward the window and detects reflected light on a calibration substrate or a mirror placed above the window. A cover, e.g., a shutter or an iris, protects the detector from UV radiation when not in use. The UV intensity detector must be able to withstand high UV energy. The UV detector may be a silicon carbide (SiC) photodiode or photodetector. It may also include a diffuser.

The mirror is oriented toward the detector and reflects UV radiation toward the detector. It may be detachable from the UV radiation assembly or may be configured to not interfere with UV delivery to the chamber during substrate processing. The mirror may be coated with a high temperature UV coating or a metal coating, such as aluminum coating. The calibration substrate reflects UV light in the wavelengths of interest. The substrate may be a bare silicon wafer, a wafer coated with high temperature UV coating or another appropriate coating such as aluminum.

The apparatus may also include a controller configured to execute a set of instructions. The controller compensates for measured intensity by executing instructions to measure a UV intensity at a UV radiation power, calculate a deviation based on the measurement and a baseline intensity, and adjust the UV radiation power or exposure duration to compensate for the deviation. The controller may also direct the cover to move, by executing instruction to open the cover, e.g., shutter or iris, to expose a UV detector to the UV radiation and close a shutter or iris to isolate the UV detector from the UV radiation.

In another aspect, the present invention pertains to methods of calibrating a UV apparatus. The method may be simple compensation of measured UV intensity, issuance of alarm or a warning, or determination of maintenance or corrective action. The UV apparatus calibration may be performed while the pedestal remains hot and the chamber under vacuum, i.e., without shutting down or removing the system or chamber from service. The method includes receiving a calibration indication or determining that a calibration is required; positioning a calibration substrate on a substrate holder; setting a UV radiation power to a first power; measuring a UV detector output over a duration; and, removing the calibration substrate.

The calibration indication may be triggered in software by duration of exposure, total intensity, time lapse, number of wafers processed, etc or be triggered manually by an operator.

A calibration substrate is provided to the chamber on a substrate holder. This calibration substrate may be kept in a front opening unified pod (FOUP) in the plant's substrate warehouse system or in a storage locker. The calibration substrate may be a bare silicon wafer with certain UV reflectivity or be coated. Appropriate coatings are those that can withstand periodic UV exposure with minimal change in UV reflectivity. Appropriate coatings may include high temperature UV coating and deposited metal, such as aluminum.

After the calibration substrate is positioned on the substrate holder, it is exposed to UV radiation at a first power, which may be chosen by the operator. The first power may be at 50%, 75% or 100% power. The UV radiation reflects off the calibration substrate back through the window and is measured by the UV detector over a duration of time. At the end of the measurement duration, the UV power may be turned off, the UV detector may be blocked from radiation, or the signal measurement may simply stop. The calibration substrate may be removed after the measurement duration.

The method may also include operations to open and close a cover that protects the UV detector from effects of continuous exposure to the UV radiation during normal processing. This cover may be actuated remotely through a controller to an open or a close position.

The method may also include calculating a UV intensity based on a the UV detector output measured and calculating a deviation based on the calculated UV intensity and a baseline intensity, and adjusting the UV radiation power or exposure time to compensate for the deviation. UV radiation generated by a lamp first passes through the chamber window to the substrate, a portion of the radiation reflects off the substrate then back through the window before it is detected by the UV detector. Thus the radiation intensity detected at the detector is not the same as that experienced by the substrate. A controller may be programmed to take into account the reflectivity of the substrate at various UV wavelengths to arrive at a UV intensity. This intensity only needs to be comparable from test to test. It may be a normalized value based on some maximum, it may be an absolute value in watts per centimeter squared ($W/cm^2$). In some cases, the raw detector output may be used as indication of intensity. This measured UV intensity is compared to a desired value and corrective action taken to compensate for a deviation. For example, if the measured UV intensity is lower than desired, than UV power may be increased or exposure time may be increased if power cannot be further increased. If the measured UV intensity is more than desired, than UV power and exposure time may be correspondingly adjusted.

In certain embodiments, the method may also include positioning a mirror between a process chamber and the UV detector, measuring the reflected UV radiation, and determining whether the process window between the mirror and the substrate requires a cleaning. The difference between reflected UV radiation from the mirror and from the substrate is the path. The reflected UV radiation from the substrate passes through the chamber window twice, whereas the UV radiation from the window does not. Knowing the reflectivity of the mirror and the substrate, the controller calculates a difference that is attributable to the window. As discussed some UV curing results in gaseous byproducts that can deposit on the window and obscure it. If the difference attributable to the window is greater than a predetermined amount, then a signal to clean the window, either automatically through the system control or manually through an alarm or warning to the operator, is generated.

Other required maintenance or corrective activity may be determined. This determination may be in the form of an alarm or warning to the operator, or even logs associated with a batch of wafers processed. Particularly, the activity may be to replace UV lamps if the measured UV intensity too low to be compensated by lengthened process time. In addition to cleaning the window, the chamber itself may require cleaning or the detector may need to be replaced.

These and other features and advantages of the invention will be described in more detail below with reference to the associated drawings.

DETAILED DESCRIPTION OF A PREFERRED EMBODIMENT

Introduction

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Reference will be made in detail to implementations of the present invention as illustrated in the accompanying drawings. The same reference indicators will be used throughout the drawings and the following detailed description to refer to the same or like parts. In this application, the terms "work piece," "wafer" and "substrate" will be used interchangeably. The following detailed description assumes the invention is implemented on a wafer. However, the invention is not so limited. The work piece may be of various shapes, sizes, and materials (e.g., displays of various sizes).

The present invention involves an ultraviolet (UV) irradiation apparatus for processing semiconductor substrates. UV radiation is used to treat thin films on substrates to achieve various property changes. UV radiation can break chemical bonds, change composition of material, cause chemical reactions to occur, affect density and stress, and otherwise provide energy to a substrate.

A typical implementation of UV irradiation apparatus has a number of UV lamps to illuminate a substrate. The UV lamps may be flood lamps, generating UV light in a broad range of wavelengths, or a high intensity discharge light that emits UV radiation in a smaller spectrum. Monochromatic sources of UV radiation, such as certain lasers, may also be used. Lamps may be powered through excitation by electrodes or microwave energy and may be inductively coupled.

In certain implementations, two individual linear mercury bulbs are used in two individual lamp assemblies. With a two-bulb configuration, the relative orientation of the bulbs to the circular substrate is varied over time to achieve a uniform exposure for each circular section. Various reflectors are also used in lamp assemblies to direct generated UV radiation toward the substrate. Linear bulbs generate light in all directions, but the substrate surface is only on one side of the bulb. Thus reflectors are used to direct UV radiation that would have otherwise escape from the lamp assembly toward the substrate. This way, lamp power is used more efficiently. In other implementations, the bulbs may be of different shapes, e.g., light bulb shape or toroidal.

In order to achieve the various film property changes on a substrate, the amount of curing that occurs as result of exposure to UV radiation must correspond to the amount of property changed desired. Thus for some property changes, a small amount of cure is required and for others, a larger amount of cure is required. The amount of UV cure is a function of UV radiation intensity, substrate temperature, and in some cases pressure and the gas present in the chamber. To ensure that the amount of film property change is constant from one substrate to another, the amount of cure must be controlled over time to ensure wafer to wafer uniformity.

Reliable methods are known to control substrate temperature, chamber pressure, and the gas present in the chamber. The substrate may be heated or cooled during the UV exposure. This heating or cooling may occur by controlling the temperature of the pedestal on which the substrate is positioned or by adding gas into the chamber at a certain temperature. Chamber pressure is controlled through vacuum pumps or common vacuum forelines and pressure gauges. The gas in the chamber may be controlled by first evacuating the chamber then adding whichever gas is desired. During some UV treatments, the gas in the chamber may actively participate in the changing of film properties by reacting with the film.

UV radiation intensity is also controlled. UV radiation intensity as experienced by the substrate depends on a number of factors. The power applied to the UV lamps determines how much radiation is generated at the source. The condition of the UV lamps determines how effective the power is used to generate UV radiation. The type of cooling gas in the UV lamp assembly determines how much radiation is absorbed. The design of the reflectors and the reflectivity determines how much radiation is directed through the chamber window. The type of material used for the chamber window and its cleanliness determines how much of the radiation directed at the window passes through. Finally the radiation reaches the substrate at a certain intensity.

The contribution of these factors changes over time in part because various parts of the UV lamp assembly and the chamber may become solarized over time. Solarization refers to a phenomenon where a material undergoes a change after being subjected to high energy electromagnetic radiation, such as ultraviolet light. Clear glass and many plastics will turn blue and/or degrade after long term solar exposure in the desert. It is believed that solarization is caused by the formation of internal defects, called color centers, which selectively absorb portions of the visible light spectrum. Solarization may also permanently degrade a material's physical or mechanical properties, and is one of the mechanisms involved in the breakdown of plastics within the environment. Prolonged exposure to high intensity UV light such as that used in UV cure damages chamber parts, especially those made from organic polymers and affects reflectivity over time. Some materials may be more resistant to UV-induced damage, such as Teflon, PTFE and PFA Two major factors that affect UV intensity over time at the substrate are the condition of UV bulbs and the chamber window. UV lamp bulbs used for curing are subjected to high powers, e.g., for intensities up to 1 W/cm^2, and sustain high cycling. The bulb performance degrades over time. Given the same power input, the output intensity reduces over time. In order to maintain the same intensity output, bulbs may be subjected initially to a lower power that is slowly increased over time to compensate for the decrease in performance. At some point, the bulbs are replaced. The bulbs may be replaced on certain triggering events regardless of their performance. These events may be a number of cycles, total cure time, total time, the number of substrates cured, total power, etc. The bulbs may also be replaced based on performance, for example, if the bulb does not output an expected intensity. Efficient use of bulbs and system downtime, e.g., for bulb replacement, suggests that a performance based method is preferred. However, for planning purposes, having periodic replacements that are designed to be shorter than the useful lifetimes of the bulbs ensure functioning UV bulbs and reduces the number of unscheduled downtimes.

The chamber window also affects the UV intensity at the substrate. Some UV processes involve evolution of solvents or reactions that emit gaseous by-products. One example is porogen removal. Porogen is removed from as-deposited ultra low-k (ULK) layers with UV radiation and the gaseous by-product removed from the chamber. Sometimes the by-products, usually organic contaminants, deposit on chamber parts before they can be removed. If deposited on the chamber window, they can build up over time and obscure the window to reduce the UV radiation passing through. Efforts to reduce these unwanted deposits, e.g., inert gas curtain below the window or higher purge gas flows, have not eradicated them. Thus, even if the UV bulbs are performing well, UV intensity at the substrate may still be reduced.

One attempt to address wafer to wafer cure uniformity is to measure the UV intensity at the substrate position. A lightpipe embedded in the pedestal or substrate support can measure the UV radiation from time to time. A light pipe collects radiation at the tip, usually made of sapphire, and transmits it through optical fibers to a photodetector. The change in the lightpipe measurement over time approximates that experienced by the substrate. However, the gaseous contaminants can deposit on the lightpipe and must be constantly and consistently cleaned. The constant and high powered UV exposure can solarize the lightpipe material and change its sensitivity. Embedded in the pedestal, the lightpipe is subjected to thermal cycles with the heated pedestal, which changes the transmitted value. The heated pedestal also emits infrared radiation which interferes with the light measured. Finally, the optical fiber connecting from the lightpipe has also been found solarized, which degraded the signal.

The lightpipe is periodically recalibrated as its measurements change over time. The lightpipe measures a radiance temperature that is affected by the chamber environment. Changes in the environment and the lightpipe over time can affect interpretation of its measurement unless it is periodically calibrated. As discussed above, knowing the UV intensity at the substrate position may not resolve the cause—a low UV intensity may mean bad bulb performance or dirty window or both. In one aspect, the present invention allows a periodic calibration of the lightpipe that is unaffected by the conditions inside the chamber.

In another aspect, the present invention is a method of calibrating a UV apparatus. The measurements from the in-situ UV detector of the present invention may be used to calibrate the UV apparatus independently of the lightpipe.

The in-situ detection and detector assembly apparatus avoid many of the problems of the lightpipe. The in-situ detector is mounted outside of the chamber, thus it is immune to any gaseous contaminants depositing on the detector. In certain embodiments, it is protected from solarization effects by a shutter mechanism that only opens during measurement. It is protected from thermal cycling by nitrogen purge gas and shielded from pedestal-emitted infrared radiation emitted by the calibration substrate. In some embodiments, the measured value can be used to determine the exact remedial/maintenance action required, because the effects of a dirty window can be isolated. Reflecting UV radiation to an outside UV detector is advantageous because it can be done under normal UV cure operating conditions. A calibration substrate can withstand substrate support temperatures of 400° C. or greater and can be inserted automatically using system controls. A calibration can immediately follow UV processing, without waiting for the pedestal to cool or chamber to be opened. Since chamber vacuum and temperature are maintained, time required to return the chamber to service is also reduced.

Figure 1A:
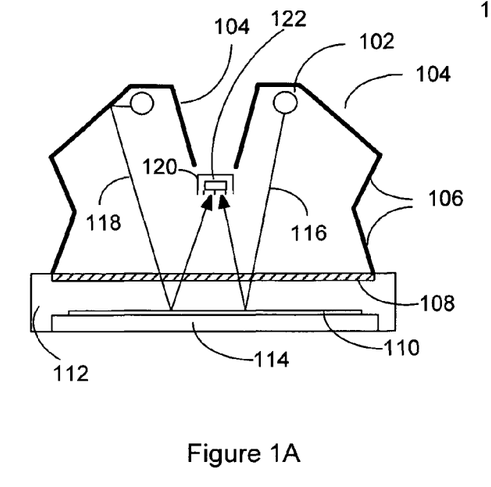
FIGS. 1A to 1D are schematics of UV lamp assembly with in-situ UV detector assembly and mirror in various positions.

FIG. 1A shows a cross section schematic of one implementation of two lamp assemblies using an embodiment of the present invention. The schematic of FIG. 1A shows a configuration while a UV measurement takes place. Lamp assemblies are mounted over a process chamber 112 over window 108. Linear bulbs 102 generate UV radiation in all directions. Some of the generated radiation directly irradiates the calibration substrate 110 which is supported by substrate support 114. Some of the radiation is reflected off various reflectors before irradiating the substrate. Overhead reflectors 104 surround the bulb and redirect radiation toward the substrate. The ring reflector 106 surrounds the space above the process chamber window 108. A UV detector 122 is positioned inside a detector assembly 120. As shown in FIG. 1A, light ray 116 from the bulb 102 is reflected off the calibration substrate 110 to the UV detector 120. A light ray may also be reflected first from a reflector before reaching the substrate, such as light ray 118. Light rays 116 and 118 are both detected by detector 122. Note that before reaching the detector, the light passes through the window 108 twice.

Figure 1B:
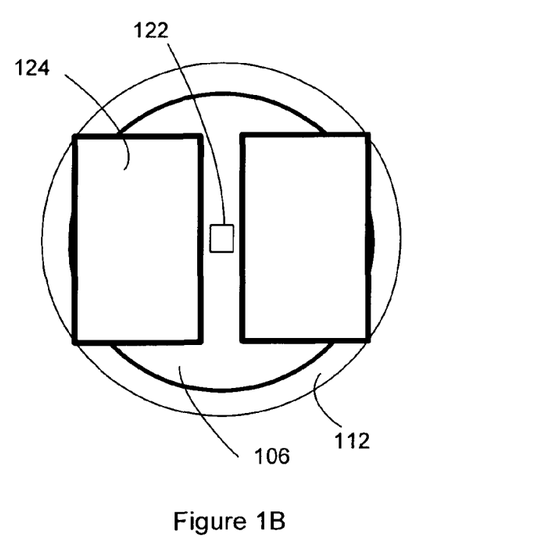

FIG. 1B shows a top view of the same lamp assembly as FIG. 1A. Lamp assembly housings 124 enclose tubular bulbs 102 and overhead reflectors 104 and are rectangular in shape. They are mounted over ring reflector 106 which sits over the process chamber 112. The detector 122 is situated in between the lamp assembly housings and below the bulbs.

Figure 1C:
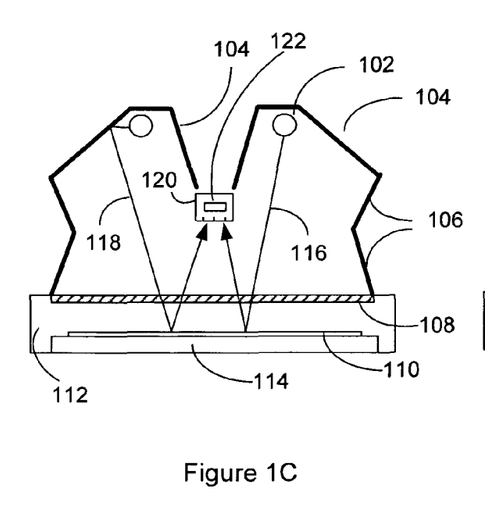

FIG. 1C shows the detector assembly 120 in the shut position. Just like in FIG. 1A, UV light reflected from the calibration substrate 110 reaches the detector assembly, but note that the light does not reach the detector 122. The detector assembly 120 has a closed cover that protects the UV detector from reflected radiation during, for example, UV curing of substrates. As required when a measurement takes place, the cover can then open to expose the detector to the UV radiation.

Figure 1D:
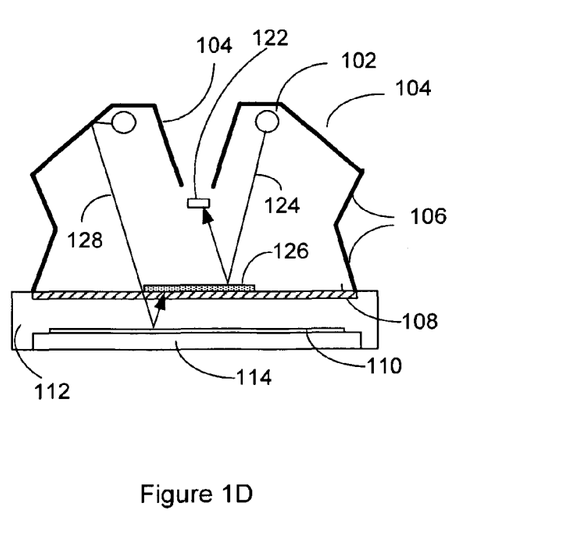

In FIG. 1D, a mirror 126 is positioned on top of the process window to take another measurement. For this measurement, only UV light reflected from the mirror is measured, for example, light ray 124. This measurement removes the effect of window cleanliness from the result because light ray 124 does not pass through the window 108 at all before being detected. As an example, light ray 128 is prevented from reaching the detector because of the mirror 108 in its path. Thus the pass-through rate of the window is removed from this measurement.

Results from the measurement of FIG. 1A over time correspond to the UV intensity as seen by the calibration substrate. However one must note that this intensity differs from that of the light pipe described above because one more pass through the window is included. Results from the measurement of FIG. 1D over time correspond to a condition of the UV bulbs 102. Because the effects of the window deposits are removed, this measurement gives a good indication whether the bulbs perform as expected. The difference in deviation over time between, say, time A and B for the measurement of FIG. 1A and time A and B for the measurement of FIG. 1D indicates how much the chamber window reduces UV transmission. For example, if the measurement from FIG. 1A shows a 75% decrease over a time period, but the measurement from FIG. 1D shows only a 90% decrease over the same time period, then the additional 15% must come from passing through the window. A trigger can then be set below which the window must be cleaned.

Process

Figure 2A:
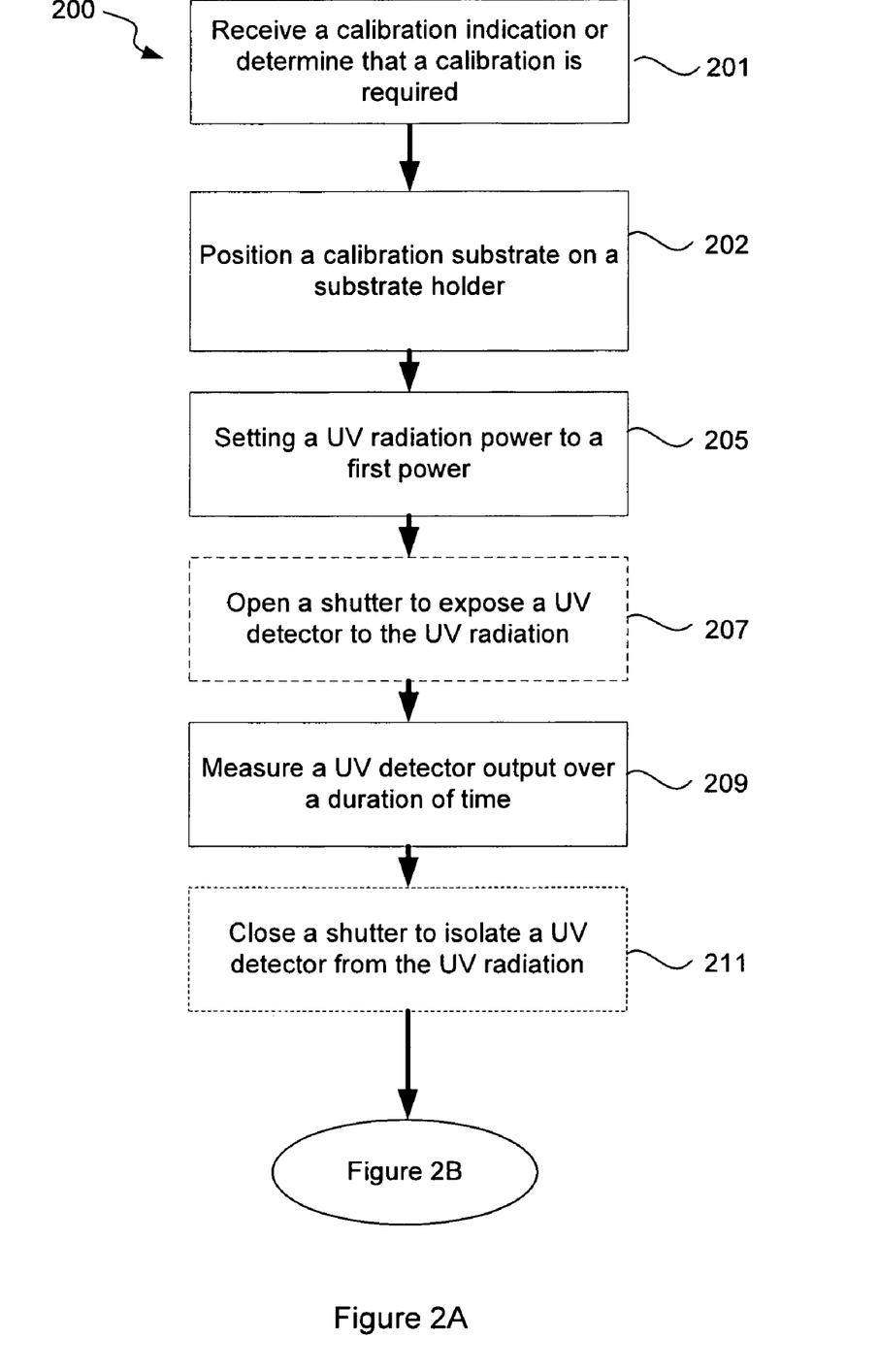
FIGS. 2A and 2B are schematics of in-situ UV detector assembly in different views in accordance with certain embodiments of the present invention.
Figure 2B:
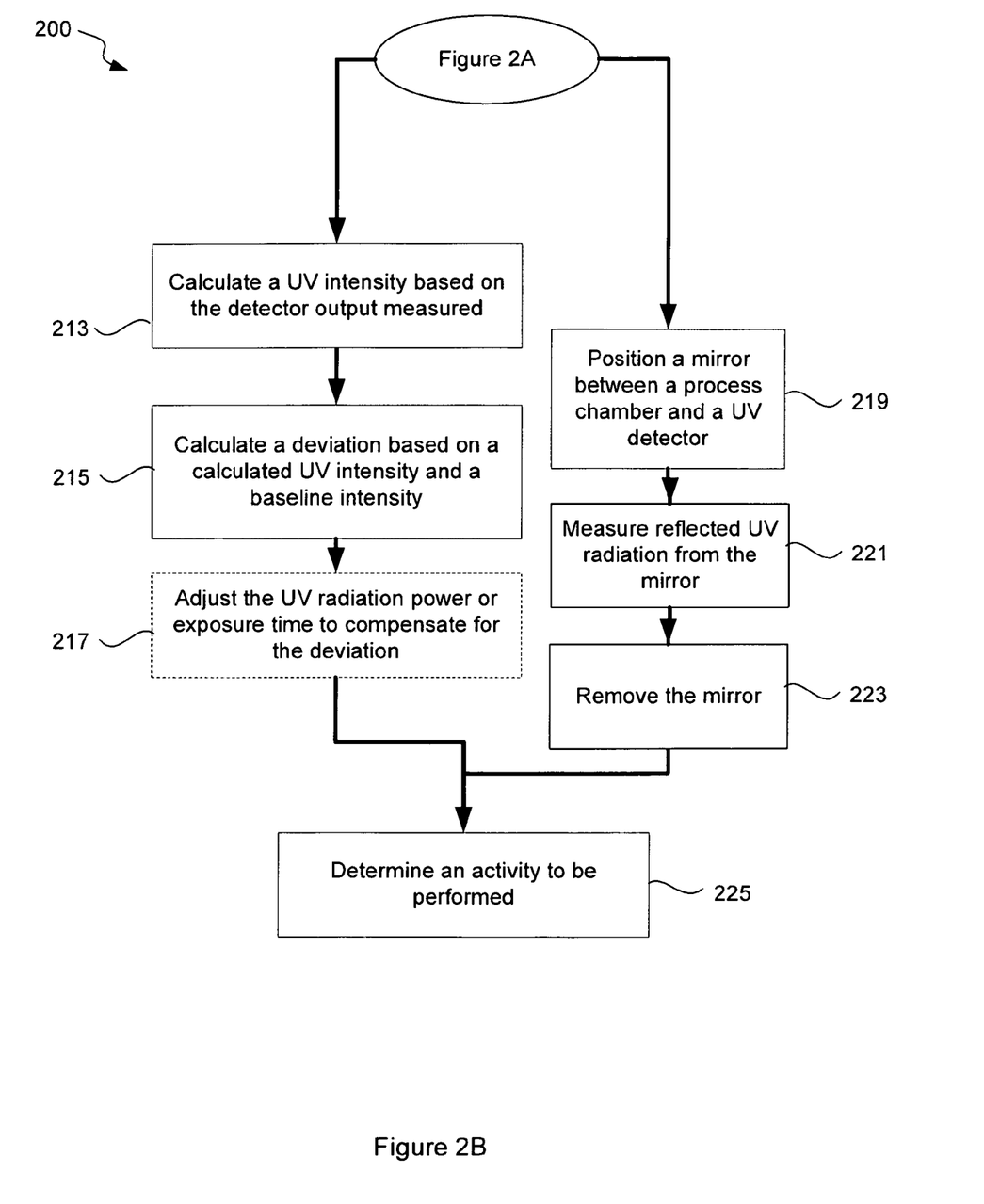

In one aspect, the present invention pertains to a method to calibrate a semiconductor UV cure apparatus. FIGS. 2A and 2B are process flow diagrams showing certain embodiments of the present invention. The calibration usually occurs after a triggering event. In operation 201, a calibration indication is received or that a calibration requirement is determined. A calibration indication may be received from an operator or the system from a downstream process that determined an unacceptable wafer-to-wafer uniformity. An indication from an operator may be initiated as part of preventive maintenance or as part of trouble-shooting to resolve UV intensity loss.

Alternatively, a calibration requirement may be determined, such as the control system determining that a triggering event has occurred. A triggering event may be based on accumulation of a consumption-based variable, a performance-based measurement such as UV intensity from a light pipe, or an absolute number of time or substrates processed. A variable indicating consumption of UV bulbs may be total power. UV bulbs may have life expectancies measured in terms of total power. An example of an accumulation of a variable event may be total power consumption from the lamp assemblies. The total power consumed may occur over many or a few substrates processed, over a long duration or very short amount of time. This kind of indication mirrors consumption of consumable life, but is harder to keep track of or calculate than other kinds of indications. Another kind of indication is a measurement that indicates performance. In this case the measurement may be UV intensity from a lightpipe. A change in lightpipe measurement within a few substrates processed or within a few hours may indicate a change in performance of the UV bulbs or the window transmission. As discussed above, other variables affect the lightpipe measurement so it alone cannot be used to determine remedial action. The last kind of indication may be passage of time or number of substrates processed. This kind of the indication is not directly related to the consumption of life expectancy, but may be used instead when a consumption-based variable is hard to measure or calculate. To illustrate, a calibration trigger may occur every 8 hours regardless whether any substrates were processed. A calibration trigger may also occur after every 100 substrates processed regardless of whether the processing was for 15 minutes or for 15 seconds.

The calibration is initiated by positioning a calibration substrate on a substrate holder, in operation 203. A calibration substrate reflects UV radiation into the detector during measurement. The reflectivity of a substrate at various UV wavelengths is known and changes little over time. The UV detector measurement from the same substrate can be compared and difference in UV intensities determined. The substrate may be a bare silicon wafer or a coated silicon wafer. The coating may be high temperature UV coating that is resistant to UV radiation and high temperatures, for example, metal or metal oxide. Dielectric coatings applied with ION beam assist may be able to withstand a 400° C. operating temperature and may be suitable for this application.

In one embodiment, more than one calibration substrates having different reflectivities in the UV wavelengths of interest are used. The intensity measured from two substrates may be compared to isolate the intensity measurement at the UV wavelength or wavelengths of interest. In a simple example, two otherwise identical substrates may be made, but one substrate may have a dielectric coating designed to absorb UV radiation at 250 nm (0 reflectivity). By comparing the intensity measured, the UV intensity at 250 nm may be isolated. This technique may be expanded to measure UV intensity at more than one wavelength of interest and may even involve more than two calibration substrates. In some UV cure processes, the desired reaction occurs with radiation at particular wavelengths. For those processes, knowing the intensity at a particular wavelength may be important.

When not in use, the calibration substrate may be kept in the semiconductor processing system or outside of the system. For example, the substrate may be stored in a front opening unified pod (FOUP) close to the semiconductor processing apparatus or in the fabrication plant's wafer storage system. Additionally, the apparatus may include a slot for storing the calibration substrate that is accessible to the system robot arms.

The UV radiation power is set to a first power value in operation 205. This first power may be 100% power. Preferably, the UV intensity measurements are taken at the same power value for ease of comparison. The UV lamp may be on or off when the calibration substrate is positioned, and in some cases the UV lamp may be already set to the first power value.

In certain embodiments, the UV detector is protected by an assembly that opens and closes a cover to sequentially allow UV detection and to isolate the detector from UV radiation. This cover may be a shutter or an iris. In optional operation 207, a shutter is opened to expose the UV detector to UV radiation. During the time the cover or shutter is open, the UV detector measures the radiation and provide an output, in operation 209. This output is read or measured over a duration of time. Once the measurement is complete, the shutter may be closed to isolate the UV detector from the UV radiation, in operation 211.

Operations 203 to 211 may be repeated during the calibration. As disclosed above, more than one calibration substrate may be used, thus requiring a repeat of the measurement operations. The measurement may also be repeated using a mirror between the UV detector and chamber window, as further explained below in operation 219 and 221.

FIG. 2A is continued on FIG. 2B. In operation 213, a UV intensity based on the detector output measured in operation 209 is calculated. The UV detector output may be a current or a voltage. The current or voltage is converted to an equivalent UV intensity, which may be watts per square centimeter or just a percentage of maximum. In operation 215, a deviation between the calculated UV intensity and a baseline intensity is calculated. The baseline intensity is the expected value for the power level. Based on the deviation, an adjustment of the UV cure process parameters may occur. If the deviation is very small or none, no adjustment needs to be made. However, if the deviation is in a range where adjusting the UV radiation power or exposure time may efficiently compensate for the deviation, then the adjustment may be made in operation 217. For example, if the measured intensity is higher than the expected baseline intensity, then the UV radiation power may be reduced to effect the same UV intensity. More commonly, the measured intensity is lower than the expected baseline intensity. The preferred adjustment may be to increase the UV radiation power, if the power is not already at the maximum. If the power is already at the maximum, then the exposure time may be increased to compensate for the deviation. Note that increasing exposure time decreases system throughput, which is undesirable. Thus this adjustment may be made deliberately if the resulting throughput is within desirable limits.

Optional measurements using a mirror to isolate the effects of chamber window deposits may be made before, at the same time or after the calculation operations and the calibration substrate measurement. A mirror may be positioned between a process chamber and a UV detector, in operation 219. In some embodiments, this mirror positioning may be performed mechanically by using a robot arm or a solenoid. In other embodiments, an operator may perform this mirror positioning while the UV bulb is off. For example, a door on the side of the lamp assembly may be opened and a mirror inserted into a slot. The mirror is highly reflective of UV light. In certain embodiments, it may be a portion of a calibration substrate that is the same as one used inside the chamber. It other embodiments, it may be a piece of metal or glass coated with reflective material.

In operation 221, a UV intensity measurement is taken to measure reflected UV radiation from the mirror. This operation may be performed by repeating operations 205 to 211. During the measurement, whether the calibration substrate is on the substrate holder is not important because light reflected from the substrate is not measured. After the UV intensity is measured, the mirror may be removed in operation 223. Similar to the positioning operation, the mirror may be removed mechanically or by operator and automatically or manually.

As disclosed above, the UV intensity reflected from the mirror may be used to determine a cleanliness of the process window. From the window cleanliness and the deviation calculated in operation 215, a number of maintenance activities may be performed. In operation 225, the activity to be performed is determined. For example, if the window cleanliness accounts for most of the deviation, then the window is cleaned, either through a remote plasma clean or dissembling the chamber and manually cleaning the inside. In another example, if the deviation is not caused by window cleanliness, then the UV bulbs may be replaced. Because dissembling the chamber requires shutting down the entire system and takes a lot of time, it is avoided if possible. Knowing the deviation and whether the window is dirty allows the operator or the system to determine the best maintenance activity that minimizes downtime.

Other operations may be performed in addition to those of FIGS. 2A and 2B. For example, a comparison of UV intensity measured with different calibration substrates, as discussed above, may be done to resolve UV intensity at particular wavelengths that is important to the process. Other ways to resolve UV intensity at particular wavelengths may include using wavelength specific detector and adding a filter between the detector and the window. One skilled in the art would be able to design various ways to measure UV intensity overall, at different bands, or at specific wavelengths using the concepts disclosed herein.

Apparatus

Figure 3A:
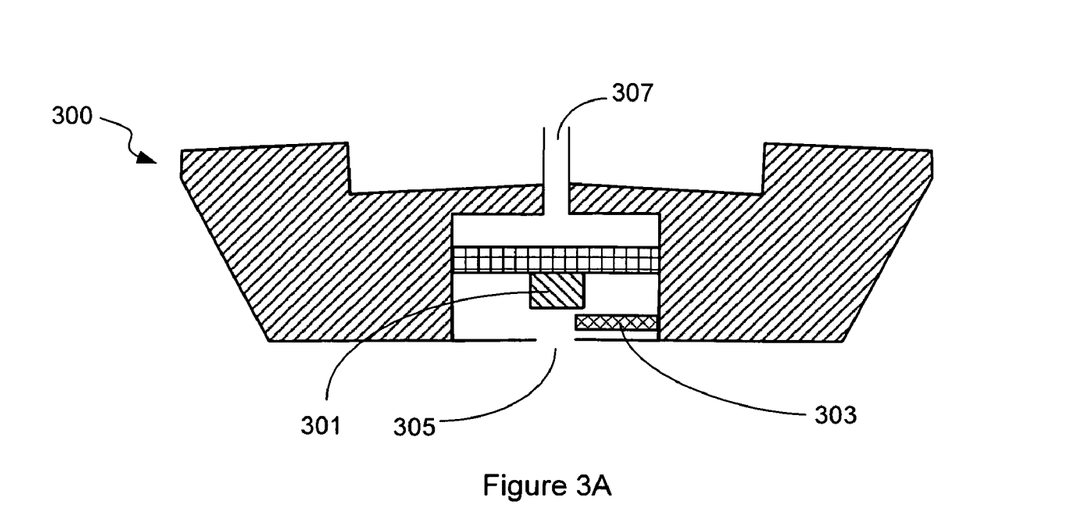
FIGS. 3A and 3B are process flow diagrams depicting a process in accordance with certain embodiments of the present invention.
Figure 3B:
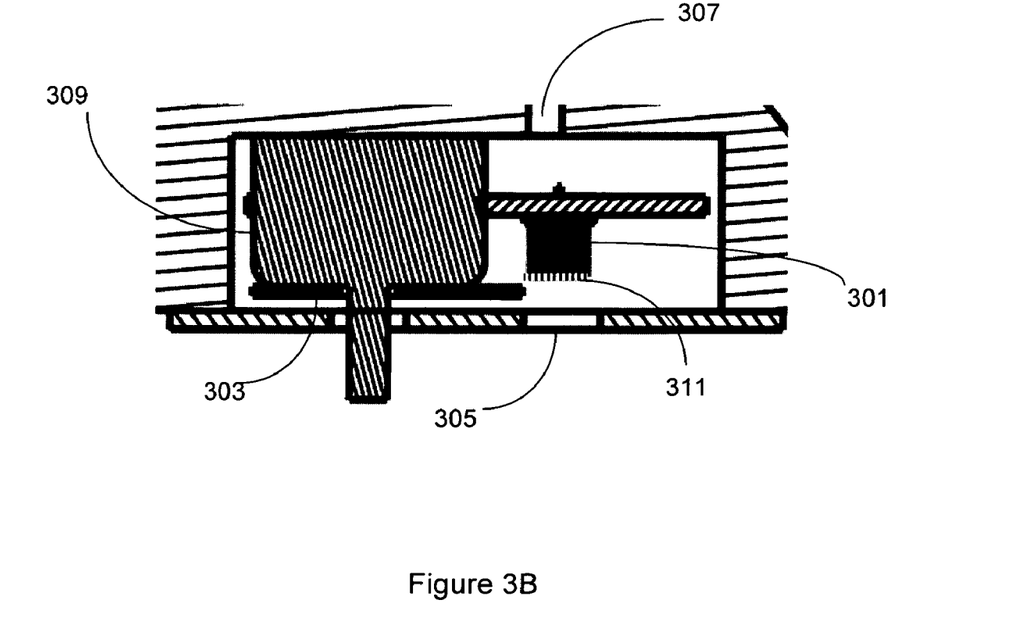

FIGS. 3A and 3B shows more detail in one implementation of the detector assembly from different views. In FIG. 3A, the UV detector 301 is located inside the assembly 300. The detector 301 faces an opening or slot 305 through which reflected UV radiation may enter the assembly. A cover 303 may be moved to cover the opening or slot 305 to isolate the UV detector 301 from reflected UV radiation. During UV lamp operation, inert gases such as Argon or Nitrogen, at about 1-10 slm, flow into the assembly through inlet 307 to cool the assembly and to remove any particles that result from the moving cover. The inert gas is preferably Nitrogen, which may be at room temperature or cooled. The gas exits the assembly below the cover.

FIG. 3B shows the assembly of FIG. 3A in a side perspective. The UV detector 301 show also includes a diffuser 311 installed on its face. The diffuser integrates light from different directions and is known in the art. Inert gas injected from inlet 307 exits the assembly below the cover 303. As shown, a small gap exists between the cover and the bottom of the UV detector assembly.

In the embodiment shown on FIG. 3B, a solenoid 309 rotates the cover 303 in place to cover the opening 305 for isolating the detector 301 or out and away to expose the detector 301 to reflected UV radiation. In other embodiments, other mechanical means may be used to effectuate the covering and uncovering of the opening. For example, the cover or shutter may be moved by a lead screw or a stepper motor. The cover also may be an iris with multiple pieces that rotate at the same time. A suitable mechanism is remotely controllable either electronically or mechanically from outside of the lamp assembly.

Figure 4:
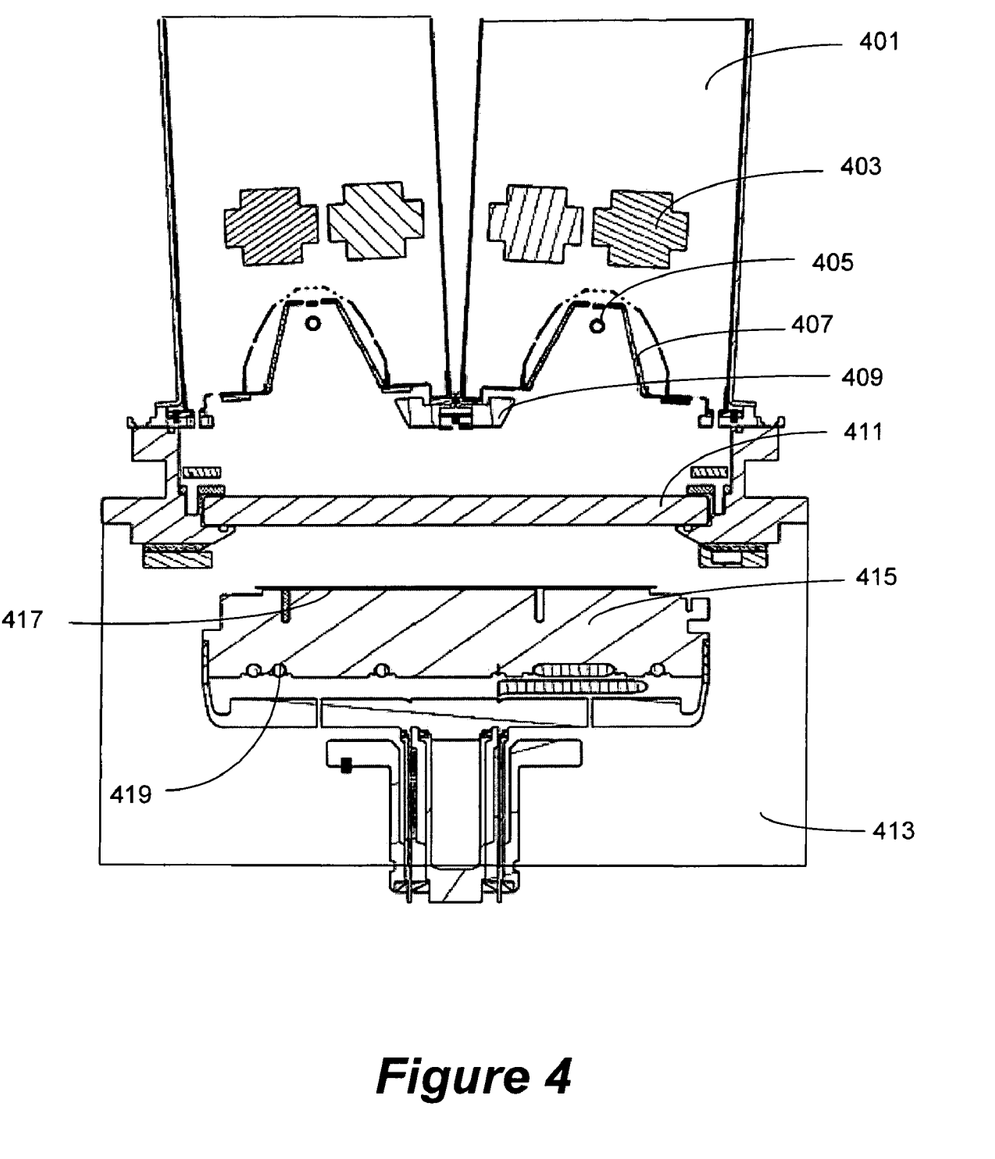
FIG. 4 is a cross-section schematic of a UV lamp assembly and chamber in accordance with certain embodiments of the present invention.

FIG. 4 is a schematic of a process chamber suitable for practicing the present invention. UV lamp assemblies 401 are mounted on top of process chamber 413. Each lamp assembly 401 includes transformers 403 and magnetrons (not shown) that pump microwave energy into the lamp, UV bulb 405, and reflectors 407. As shown, the UV detector assembly 409 is mounted below and between two lamp assemblies 401. A chamber window 411 transmits UV radiation from the bulbs 405 to the substrate 417 below in the chamber. The substrate 417 sits on a substrate support 415, which may be heated, cooled or both. As shown, a heater coil 419 is embedded in the substrate support 415.

Figure 5A:
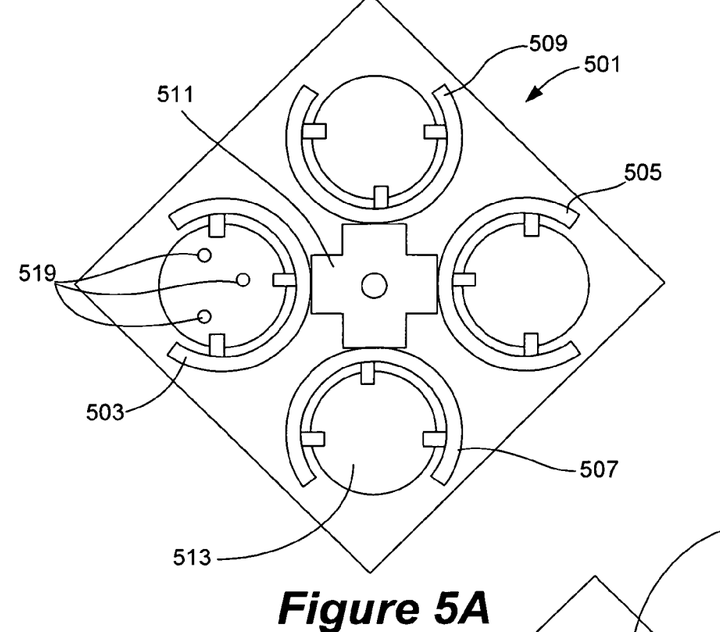
FIGS. 5A and 5B are schematics of a multi-station UV cure chamber in accordance with certain embodiments of the present invention.
Figure 5B:
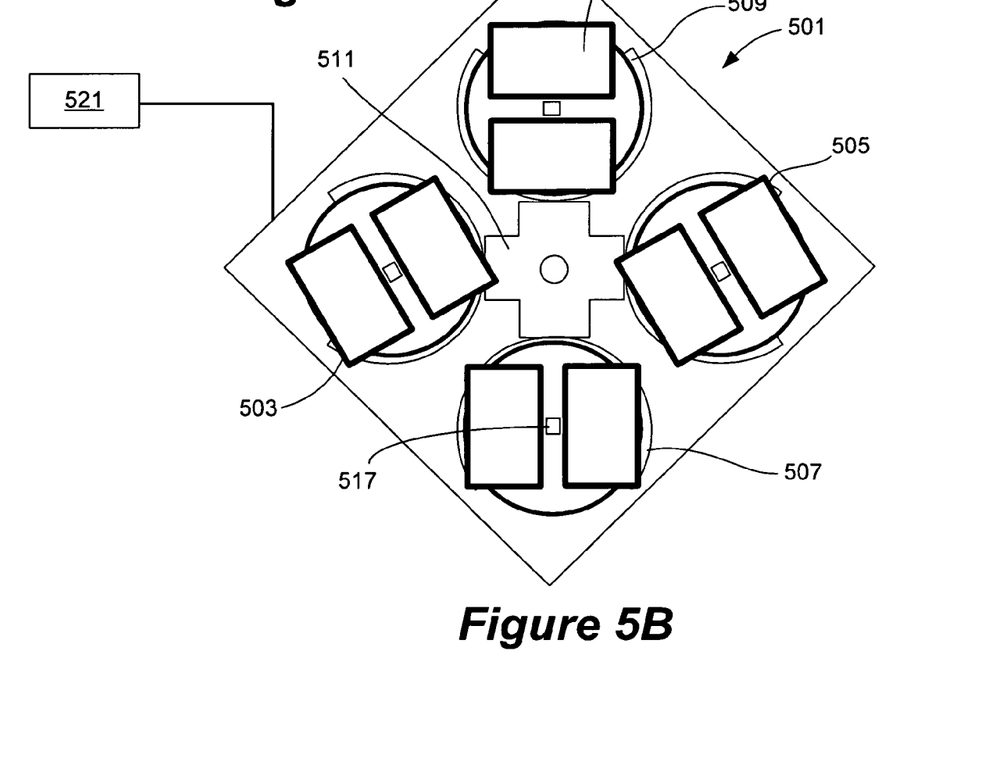

In some embodiments, the process chamber includes multiple stations each having a substrate support, chamber window, and UV lamp assemblies. FIGS. 5A and 5B are schematics of a multi-station chamber suitable for practicing the present invention. Chamber 501 includes four stations 503, 505, 507, and 509. Each station includes a substrate support 513. Embedded in the substrate support 513 are pins 519. Four carrier rings are connected to a spindle 511 that rotates about an axis. When a new substrate is introduced into a chamber, for example, at station 507, it is positioned on a robot arm. The carrier ring lowers the substrate to the substrate support, where it sits on top of the pins 519. After substrate processing is complete at one station, the carrier ring lifts the substrate and rotates 90 degrees to the next station, where it lowers the substrate for processing. Thus a substrate enters the chamber at station 507 sequentially moves through each of the four stations before exiting the chamber.

FIG. 5B shows a top view of the same multi-station chamber with UV lamp assemblies 515 on top of each station. The UV detector assembly 517 is positioned about the center between two lamp assemblies. Note that the lamp assemblies have a different relative orientation to the substrate as the substrate moves through each station. This different relative orientation ensures that each circular section of the substrate is exposed to the same amount of UV radiation. Because the UV bulb is tubular and substrate is round, in each station different parts of the substrate receive differing amounts of UV radiation. By changing the relative orientation of the bulbs to the substrate, these differences are overcome. Generally, having four stations of varying orientation is sufficient to ensure a relatively uniform UV irradiance. Of course, the relative orientations are not limited to the one shown in FIG. 5B—multiple orientations of lamp axis can be chosen to optimize wafer process uniformity. Uniform exposure may also be achieved by rotating the either the lamp assembly or the substrate during UV cure.

In certain embodiments, a system controller 521 is employed to control process conditions during UV cure, calibration, insert and remove substrates, etc. The controller will typically include one or more memory devices and one or more processors. The processor may include a CPU or computer, analog and/or digital input/output connections, stepper motor controller boards, etc.

In certain embodiments, the controller controls all of the activities of the apparatus. The system controller executes system control software including sets of instructions for controlling the timing, mixture of gases, gas injection rate, chamber pressure, chamber temperature, substrate temperature, UV power levels, UV cooling gas and flow, remote plasma clean, and other parameters of a particular process. Other computer programs stored on memory devices associated with the controller may be employed in some embodiments.

Typically there will be a user interface associated with controller 521. The user interface may include a display screen, graphical software displays of the apparatus and/or process conditions, and user input devices such as pointing devices, keyboards, touch screens, microphones, etc.

The computer program code for controlling the UV cure and calibration processes can be written in any conventional computer readable programming language: for example, assembly language, C, C++, Pascal, Fortran or others. Compiled object code or script is executed by the processor to perform the tasks identified in the program.

The controller parameters relate to process conditions such as, for example, UV power, UV cooling gas and flow rate, process duration, process gas composition and flow rates, temperature, pressure, and substrate temperature. These parameters are provided by the user in the form of a recipe, and may be entered utilizing the user interface. The controller parameters that relate to calibration conditions may also be entered utilizing the user interface, such as the duration of exposure, the UV power setting for measurement, and location of the calibration substrate. Additional parameters may be entered during setup or installation of the UV detector assembly, such as conversion formula of the UV detector output to UV intensity, deviation threshold for bulb replacement and window cleaning, and whether UV intensities at specific wavelengths are to be determined. These additional parameters may be changed from time to time during system maintenance.

Signals for monitoring the process may be provided by analog and/or digital input connections of the system controller. The signals for controlling the process are output on the analog and digital output connections of the UV cure apparatus.

The system software may be designed or configured in many different ways. For example, various chamber component subroutines or control objects may be written to control operation of the chamber components necessary to carry out the inventive UV intensity measurement and calibration processes. Examples of programs or sections of programs for this purpose include substrate positioning code, process gas control code, pressure control code, heater control code, and UV lamp control code.

A UV lamp control program may include code for setting power level to the UV lamps, initial ramping up of lamp power, and final ramping down of lamp power. A substrate positioning program may include program code for controlling chamber components that are used to load the substrate onto a pedestal or chuck. A process gas control program may include code for controlling gas composition and flow rates and optionally for flowing gas into the chamber prior to UV cure in order to stabilize the pressure in the chamber. A pressure control program may include code for controlling the pressure in the chamber by regulating, e.g., a throttle valve in the exhaust system of the chamber. A heater control program may include code for controlling the current to a heating unit that is used to heat the substrate. Alternatively, the heater control program may control delivery of a heat transfer gas such as helium to the wafer chuck.

Examples of chamber sensors that may be monitored during UV cure and calibration include mass flow controllers, pressure sensors such as manometers, thermocouples located in pedestal or chuck, and of course, UV detectors in the UV detector assembly and in the pedestal. Appropriately programmed feedback and control algorithms may be used with data from these sensors to maintain desired process conditions.

In one embodiment, the controller includes instructions for performing calibration, adjustment of process parameters, and determining maintenance activities according to methods described above. For example, the instructions can specify the parameters needed to perform the UV cure and calibration. The instructions may include calculating results based on measurement using user-provided formulas or conversion charts, integrating measurement results over time, e.g., integrating UV intensity measurement over the exposure time, and compare the result to a pre-determined threshold value. The result of the comparison may be used in logic sequences where an alarm or warning is generated, process parameter changed, or system is shutdown.

Suitable semiconductor processing tools may be configured with one or more UV process chambers. Suitable semiconductor processing tools include the SOLA and modified VECTOR available from Novellus Systems, Inc. of San Jose, Calif. Other suitable semiconductor processing tools include the Centura and Producer available from Applied Materials, Inc. of Santa Clara, Calif.

Details of the UV lamp assembly, reflectors, process chamber window, and temperature control on the substrate holder may be found in commonly assigned co-pending U.S. application Ser. No. 11/688,695, titled "Multi-Station Sequential Curing of Dielectric Films", which is incorporated herein by reference in its entirety for all purposes.

For convenience, discussion of the UV lamp assembly and in-situ UV detector assembly focused on a two linear bulb configuration for the UV source; however, the present invention is not so limited. For example, the in-situ UV detector would work with any number of bulbs, e.g., 3, 4, or 5, in any kind of configuration, e.g., parallel or end-to-end. The in-situ UV detector would also work with other types of bulbs, not just linear bulbs. As UV bulbs evolve and techniques to build UV lamp assemblies advance, the use of an in-situ UV detector to monitor bulb performance continues to apply.

While this invention has been described in terms of several embodiments, there are alterations, modifications, permutations, and substitute equivalents, which fall within the scope of this invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention. The use of the singular in the claims does not mean "only one," but rather "one or more," unless otherwise stated in the claims.

What is claimed is:

1. An ultraviolet (UV) apparatus for semiconductor processing, the apparatus comprising:
   (a) a process chamber comprising a substrate holder and a window; and,
   (b) a UV radiation assembly external to the process chamber, the assembly comprising
      i) at least two UV lamps,
      ii) one or more reflectors operable to direct a portion of the UV radiation from the at least two UV lamps through the window towards the substrate holder,
      iii) an in situ UV intensity detector disposed between the at least two UV lamps, and
      iv) a shutter or iris configured to isolate the UV intensity detector from the UV radiation between measurements; and,
   (c) a controller configured to execute a set of instructions, the set of instructions comprising:
      opening the shutter or iris to expose a UV detector to the UV radiation;
      measuring a UV intensity at a UV radiation power with the UV detector;
      after measuring, closing a shutter or iris to isolate the UV detector from the UV radiation;
      calculating a deviation based on the measurement and a baseline intensity; and,
      adjusting the UV radiation power or exposure duration to compensate for the deviation.

2. An ultraviolet (UV) apparatus for semiconductor processing, the apparatus comprising:
   (a) a process chamber comprising a substrate holder and a window; and,
   (b) a UV radiation assembly external to the process chamber, the assembly comprising
      i) at least two UV lamps,
      ii) one or more reflectors operable to direct a portion of the UV radiation from the at least two UV lamps through the window towards the substrate holder,
      iii) an UV intensity detector positioned between the at least two UV lamps to receive UV radiation from the at least two UV lamps reflected through the window,
      iv) a cover configured to isolate the UV detector from radiation from the at least two UV lamps.

3. The apparatus of claim 2, wherein the detector is oriented towards the window.

4. The apparatus of claim 2, wherein the UV intensity detector comprises a silicon carbide photodiode.

5. The apparatus of claim 2, wherein the UV intensity detector includes a diffuser.

6. The apparatus of claim 2, wherein the UV radiation assembly further comprises a mirror disposed in between the UV intensity detector and the window.

7. The apparatus of claim 6, wherein the mirror is oriented towards the detector.

8. The apparatus of claim 4, wherein the mirror is detachable from the UV radiation assembly.

9. The apparatus of claim 4, wherein the mirror is coated with a high temperature UV coating or an aluminum coating.

10. A method of calibrating an ultraviolet (UV) apparatus, the method comrising:
  (a) receiving a calibration indication or determining that a calibration is required;
  (b) setting a UV radiation power from at least two UV lamps to a first power; and,
  (c) measuring an output over a duration of an in situ UV intensity detector disposed between the at least two UV lamps;
  wherein a chamber vacuum is maintained during the calibration and wherein the method further comprises opening a shutter to expose a UV detector to the UV radiation prior to (c); and closing a shutter to isolate the UV detector from the UV radiation after (c).

11. The method of claim 10, further comprising:
  positioning a calibration substrate on a substrate holder; and,
  removing the calibration substrate.

12. The method of claim 10, further comprising:
  (a) maintaining a substrate holder temperature.

13. The method of claim 10, further comprising:
  (a) calculating a UV intensity based on the UV detector output measured;
  (b) calculating a deviation based on the calculated UV intensity and a baseline intensity; and,
  (c) adjusting the UV radiation power or exposure time to compensate for the deviation.

14. The method of claim 10, further comprising:
  (a) determining a remedial activity.

15. The method of claim 10, wherein the first power is 100% power.

16. The method of claim 10, wherein the calibration substrate is a polished silicon wafer.

17. The method of claim 10, wherein the calibration substrate is coated with a high temperature UV coating.

18. The method of claim 10, wherein the calibration substrate is an aluminum-coated silicon wafer.

19. The method of claim 10, further comprising:
  (a) positioning a mirror between a process chamber and a UV detector;
  (b) measuring the reflected UV radiation; and,
  (c) determining whether a window between the mirror and the substrate requires a cleaning.

* * * * *

UNITED STATES PATENT AND TRADEMARK OFFICE
CERTIFICATE OF CORRECTION

PATENT NO. : 7,935,940 B1
APPLICATION NO. : 12/008149
DATED : May 3, 2011
INVENTOR(S) : E. Smargiassi Page 1 of 1

It is certified that error appears in the above-identified patent and that said Letters Patent is hereby corrected as shown below:

CLAIMS:
    1.    (column 15, line 2) change "comrising" to --comprising--.

Signed and Sealed this
Fifteenth Day of May, 2012

David J. Kappos
*Director of the United States Patent and Trademark Office*